US012678299B2

(12) United States Patent
Ju et al.

(10) Patent No.: US 12,678,299 B2
(45) Date of Patent: Jul. 14, 2026

(54) ACETABULAR CUP REMOVAL DEVICE FOR ARTIFICIAL HIP JOINTS

(71) Applicant: IMEDICOM CO., LTD., Gunpo-si (KR)

(72) Inventors: Don Soo Ju, Gunpo-si (KR); Byoung Ju Lee, Gunpo-si (KR); Tae San Kim, Gunpo-si (KR)

(73) Assignee: IMEDICOM CO., LTD., Gunpo-si (KR)

( * ) Notice: Subject to any disclaimer, the term of this patent is extended or adjusted under 35 U.S.C. 154(b) by 0 days.

(21) Appl. No.: 18/874,909

(22) PCT Filed: Jun. 16, 2023

(86) PCT No.: PCT/KR2023/008396
§ 371 (c)(1),
(2) Date: Dec. 13, 2024

(87) PCT Pub. No.: WO2024/071572
PCT Pub. Date: Apr. 4, 2024

(65) Prior Publication Data
US 2025/0367006 A1 Dec. 4, 2025

(30) Foreign Application Priority Data
Sep. 30, 2022 (KR) ........................ 10-2022-0125008

(51) Int. Cl.
*A61F 2/46* (2006.01)
*A61B 17/16* (2006.01)

(52) U.S. Cl.
CPC ........ *A61F 2/4609* (2013.01); *A61B 17/1666* (2013.01); *A61F 2002/4619* (2013.01); *A61F 2002/4627* (2013.01)

(58) Field of Classification Search
CPC ............... A61F 2/4609; A61B 17/1664; A61B 17/1666
See application file for complete search history.

(56) References Cited

U.S. PATENT DOCUMENTS

2016/0100846 A1* 4/2016 Motherway ........... A61F 2/4609
606/81
2018/0200073 A1* 7/2018 Joo ........................... A61F 2/34

FOREIGN PATENT DOCUMENTS

KR 10-2103774 B1 4/2020

* cited by examiner

*Primary Examiner* — Si Ming Ku
(74) *Attorney, Agent, or Firm* — Rabin & Berdo, P.C.

(57) ABSTRACT
The acetabular cup removal device for artificial hip joints according to an embodiment of the present invention comprises a main shaft and a cutter section that cuts the acetabular region while being rotated by the main shaft. The cutter section includes a cutter tilting unit capable of tilting along the acetabular region around an imaginary tilting axis, a cutter mounting unit coupled to the cutter tilting unit in a manner that allows relative sliding toward or away from the imaginary tilting axis, and a cutter detachably mounted on the cutter mounting unit. The cutter tilting unit comprises a first through-hole penetrating along the imaginary tilting axis, a connecting bar fixed at both ends to the cutter mounting unit, and a leaf spring fixed at both ends to the connecting bar with a central portion between the two ends.

9 Claims, 18 Drawing Sheets (a)

(b)

(c)

( a )

( b )

( a )

( b )

( a )

( b )

0°

30°

60°

90°

(a)

(b)

ACETABULAR CUP REMOVAL DEVICE FOR ARTIFICIAL HIP JOINTS

TECHNICAL FIELD

The present invention relates to a device for removing acetabular cups used in artificial hip joints.

BACKGROUND ART

In general, artificial hip joints serve as substitutes for hip joints when their function is impaired. These devices are implanted in place of the original hip joint to maintain normal activity.

Such artificial hip joints are typically composed of an acetabular cup, which is a hemispherical component with a liner that acts as a bearing and is inserted into the acetabulum of the pelvis, a stem which is fitted into the femur, and a hemispherical femoral head which replaces the femoral ball and is mounted at the end of the stem, fitting into the acetabular cup.

Patients experiencing pain in the hip joint due to conditions such as arthritis, dysplasia, trauma, or post-infection complications can replace the affected joint with such an artificial hip joint, restoring joint mobility and eliminating pain.

Meanwhile, artificial hip joints experience wear over time. The acetabular cup, which endures friction with the femoral head, is particularly prone to wear due to continuous joint usage. Prolonged wear can lead to severe issues such as osteolysis around the acetabulum in the pelvis. Consequently, technologies for removing previously implanted acetabular cups from the acetabulum have been continuously developed.

In this regard, the applicant has developed a device for removing acetabular cups for artificial hip joints, as disclosed in Korean Patent No. 10-2103774, shown in FIGS. 1 through 4. For reference, FIGS. 1 through 4 correspond to FIGS. 1, 4, 3, and 7 of the aforementioned Korean patent, respectively, with their numbering unchanged for convenience. However, the drawing numbers used in this explanation may not necessarily denote the same components as those in the subsequent description of the present invention.

The conventional acetabular cup removal device (100) operates by moving the undulating adjustment part (140) forward, sequentially tilting the cutter (1501) forward (counterclockwise), and detaching the acetabular cup from the acetabulum of the pelvis (see FIG. 4). When the acetabular cup (C) has a spherical shape (a shape cut in half along the diameter of a sphere), a cutter (1501) suitable for the radius of the acetabular cup (C) can be used for its removal (see FIG. 5(*a*)).

However, when the acetabular cup (C) has an elliptical shape (a shape cut in half along the minor axis of an ellipse), there is an issue during the cutting process where the cutter (1501) tilts towards the major axis (A) of the ellipse and becomes caught on the outer surface (marked with ★) of the acetabular cup (C) as it moves toward the apex (O) of the cup. This problem can prevent proper operation or, in severe cases, cause the cutter to break (see FIG. 5(*b*) at 60° rotation). Using a cutter with a larger radius could address this issue, but this approach results in greater bone loss for the patient.

DETAILED DESCRIPTION OF THE INVENTION

Technical Problem

The technical problem addressed by the present invention is to resolve the issues associated with conventional acetabular cup removal devices as described above. Specifically, the invention aims to provide an acetabular cup removal device for artificial hip joints, which can smoothly tilt and detach the acetabular cup from the acetabulum of the pelvis without the cutter getting caught on the outer surface of the cup, regardless of whether the acetabular cup is circular or elliptical.

Technical Solution

To achieve the aforementioned objective, the acetabular cup removal device for artificial hip joints according to an embodiment of the present invention includes a main shaft that can be mounted on a power tool and rotated by the driving force of the power tool, and a cutter section provided at the front end of the main shaft, which is capable of tilting along the acetabulum where the acetabular cup is implanted and cutting the acetabulum while being rotated by the main shaft. The cutter section comprises a cutter tilting unit capable of tilting along the acetabulum around an imaginary tilting axis, a cutter mounting unit coupled to the cutter tilting unit in a manner that allows relative sliding toward or away from the imaginary tilting axis, and a cutter detachably mounted on the cutter mounting unit. The cutter tilting unit includes a first through-hole that penetrates along the imaginary tilting axis, a connecting bar fixed at both ends to the cutter mounting unit, and a leaf spring fixed at both ends to the connecting bar, with a central portion located between the two ends.

Additionally, the main shaft comprises a cylinder member inserted into the first through-hole and having a second through-hole formed along its longitudinal direction. The connecting bar is positioned within the second through-hole, capable of sliding toward or away from the imaginary tilting axis, and the central portion of the leaf spring is supported by the inner wall of the second through-hole.

Additionally, the second through-hole has a circular cross-section, and a portion of the circumference of the connecting bar has an arc shape with a curvature radius identical to that of the second through-hole, allowing the connecting bar to make surface contact with the second through-hole.

Additionally, a remaining portion of the connecting bar, except for the portion that contacts the second through-hole, does not contact the second through-hole.

Additionally, the cutter mounting unit comprises a cutter mounting body with a third through-hole into which the connecting bar is inserted, and the connecting bar does not rotate relative to the cutter mounting body within the third through-hole but tilts in conjunction with the cutter mounting unit's tilting motion.

The remaining portion of the connecting bar consists of three sides connected at right angles to each other, and the third through-hole has a rectangular cross-section.

Additionally, the cutter tilting unit further includes a cover that encloses the cutter mounting body and is fixed to the opposing surface of the cutter tilting unit.

Additionally, the inner surface of the cover includes a groove corresponding to the outline of the cutter mounting body, and a gap is formed between the top end of the cutter mounting body and the top end of the groove in the cover.

Additionally, in the initial state, where no external force is applied to the leaf spring, a portion of the connecting bar contacts the second through-hole. When external force is applied to the leaf spring, it compresses, causing the connecting bar to separate from the second through-hole.

3

Additionally, the cover is fixed to the opposing surface of the cutter tilting unit without relative movement by a fastener secured to the connecting bar.

Effects of the Invention

The acetabular cup removal device for artificial hip joints according to an embodiment of the present invention, having the configuration described above, can achieve the following effects.

According to the embodiment of the present invention, unlike the conventional approach, even in the case of an elliptical acetabular cup, the cutter can smoothly traverse the surface of the acetabular cup, allowing the cutter section (cutter) to tilt up to the apex of the acetabular cup. This makes it possible to easily remove the acetabular cup from the acetabulum of the pelvis.

Meanwhile, the effects of the present invention are not limited to the above and also include other effects that can be derived from the configuration of the invention described below.

BEST MODE FOR CARRYING OUT THE INVENTION

Hereinafter, the embodiments of the present invention will be described in detail with reference to the accompanying drawings so that those skilled in the art to which the invention pertains can easily implement them. However, the present invention can be embodied in various forms and is not limited to the embodiments described herein.

For reference, the present invention is derived from a new configuration related to the coupling of the cutter tilting unit and the cutter mounting unit to solve the above-mentioned issues in the applicant's previously invented acetabular cup removal device for artificial hip joints (Korean Patent No. 10-2103774). Accordingly, to avoid obscuring the main points of the present invention, the following description will focus on the components directly related to the invention, while briefly describing or omitting the components unrelated to the gist of the invention.

In addition, the terms "first," "second," "third," etc., used in this embodiment, do not indicate order but are terms used to distinguish components with the same names.

Figure 1:
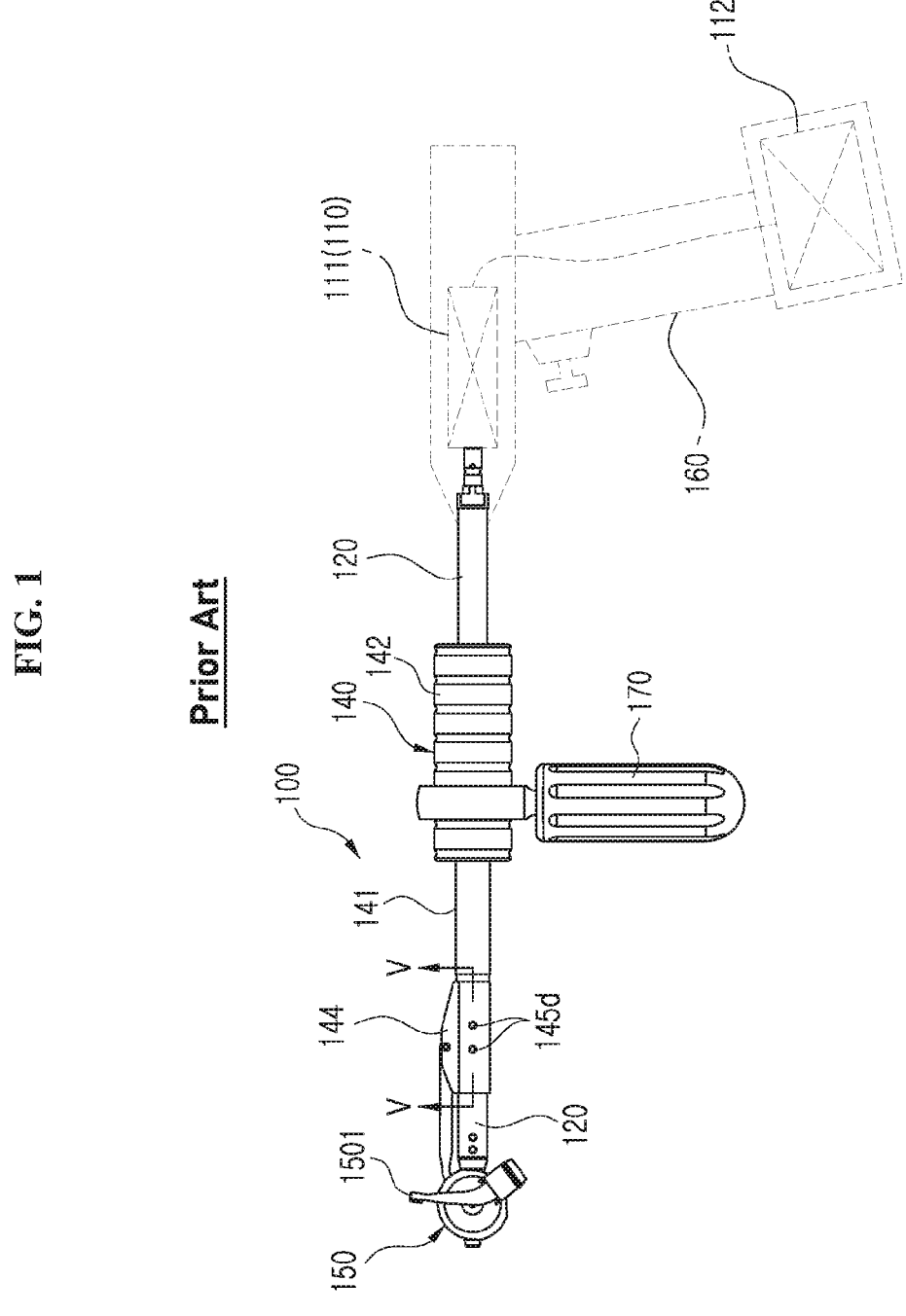
FIGS. 1 through 4 illustrate a conventional acetabular cup removal device for artificial hip joints.
Figure 2:
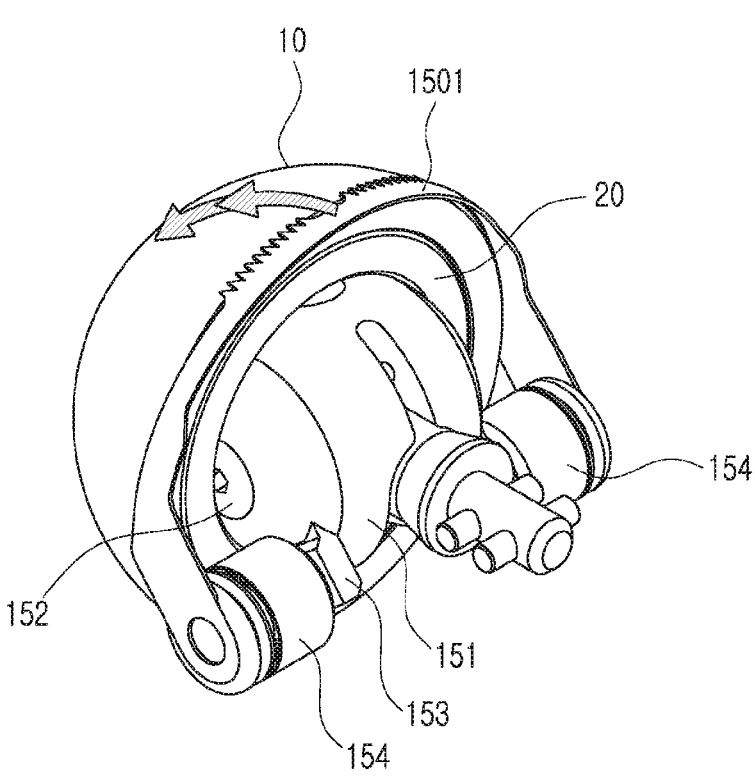
Figure 3:
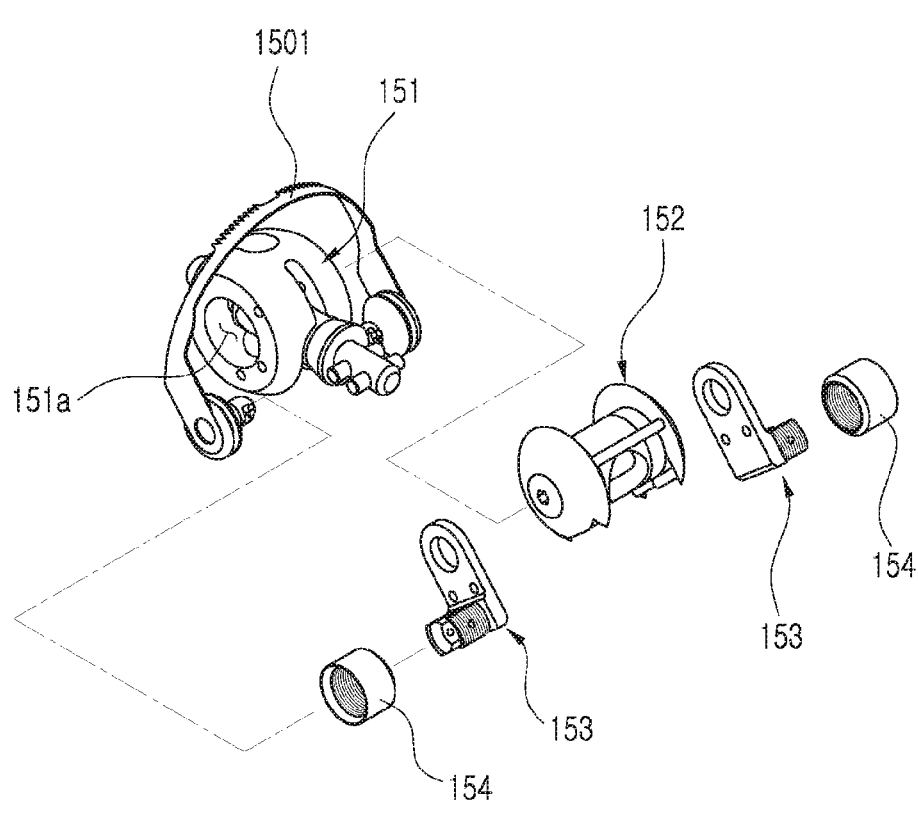
Figure 4:
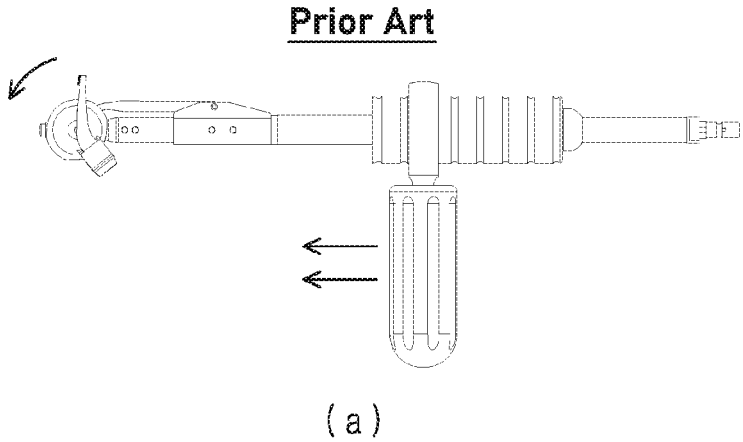
Figure 4:
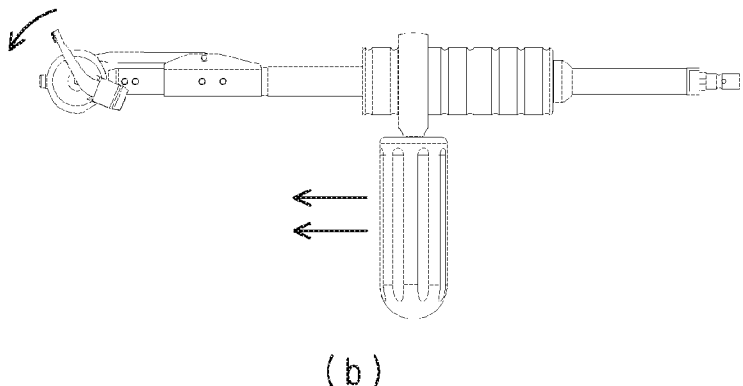
Figure 4:
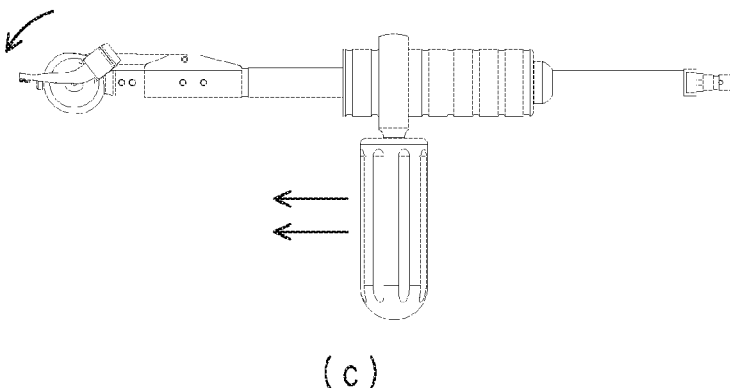
Figure 5:
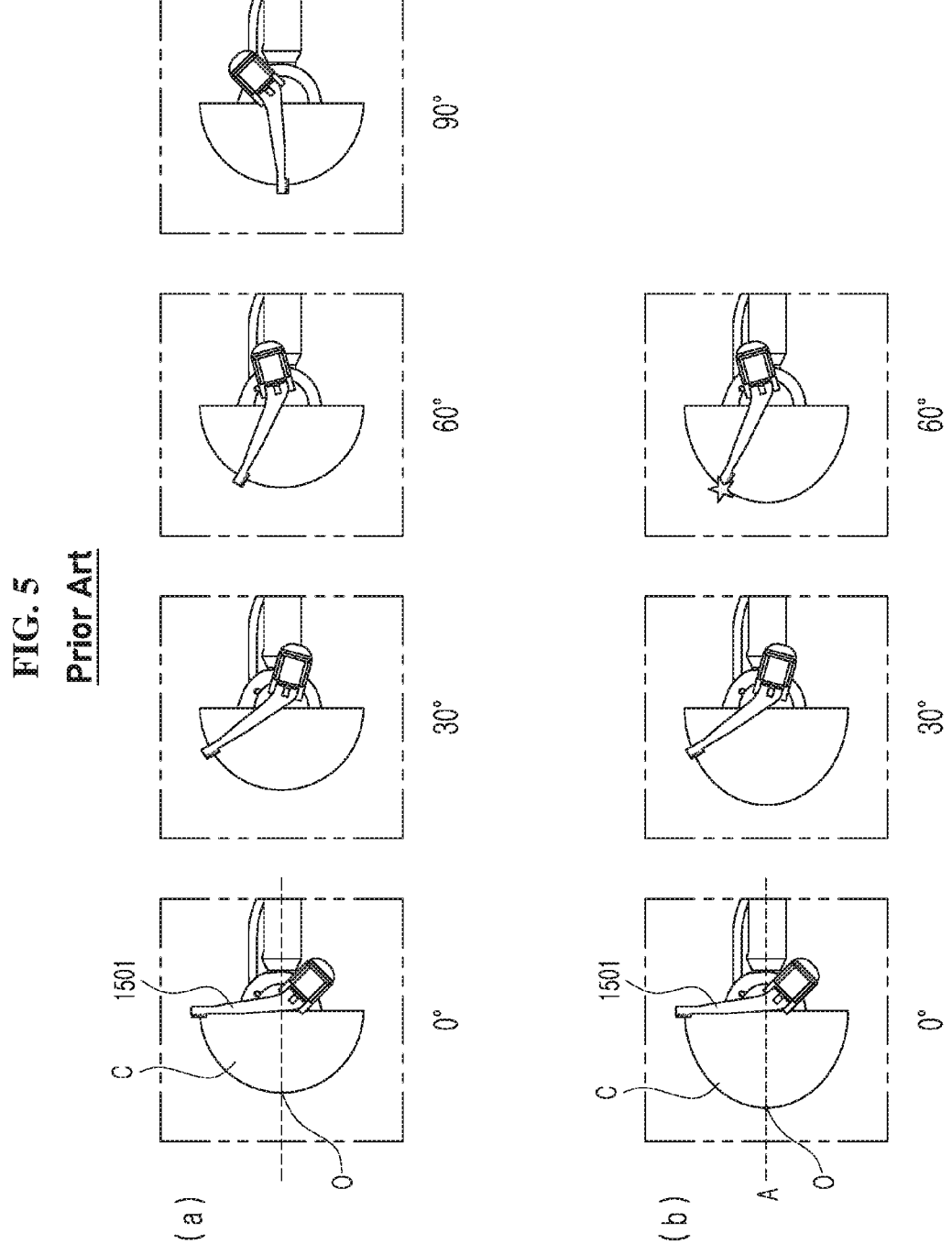
FIG. 5 is a schematic diagram showing the operation of the conventional acetabular cup removal device of FIG. 1.
Figure 6:
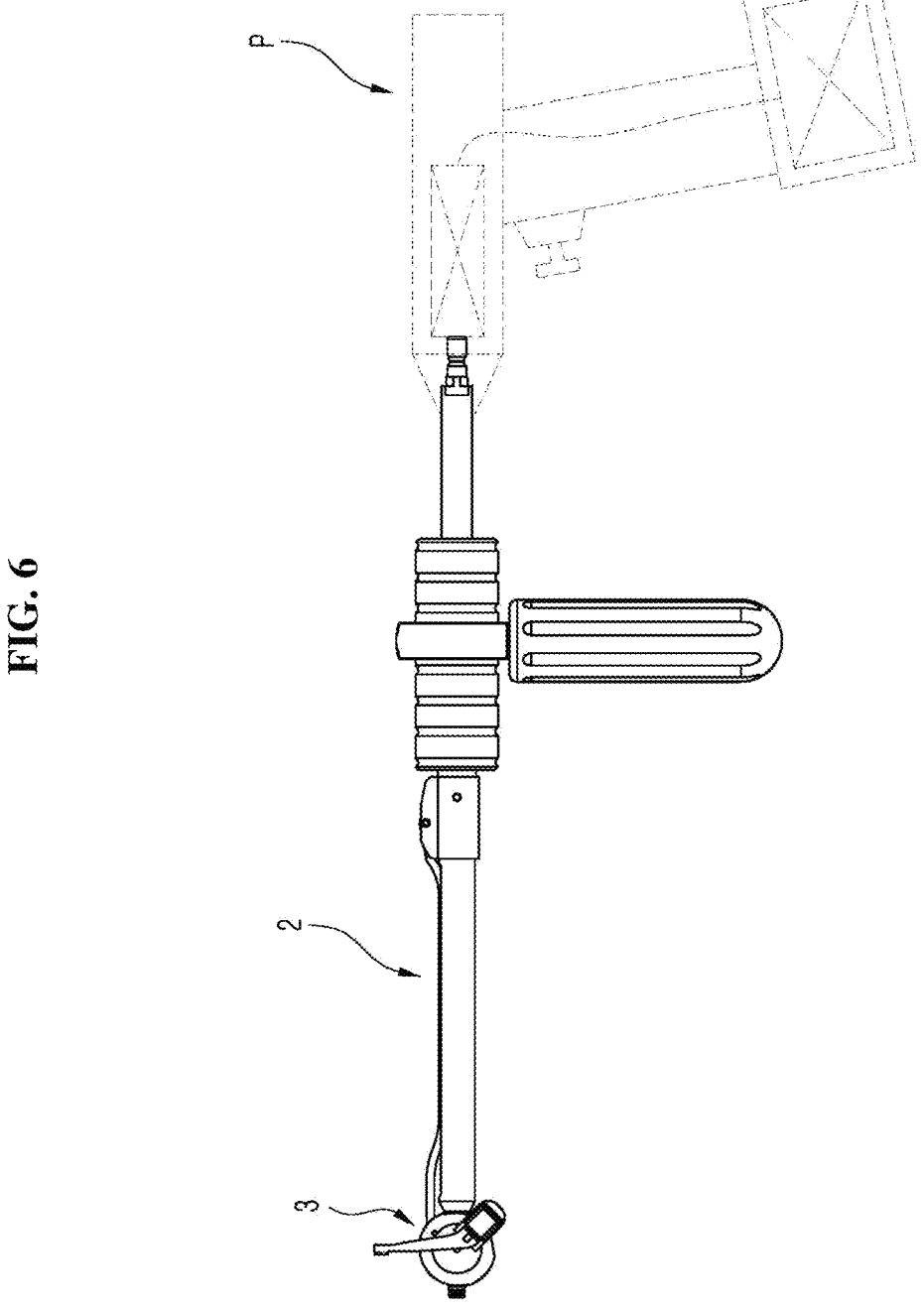
FIG. 6 illustrates an acetabular cup removal device for artificial hip joints according to an embodiment of the present invention.

As shown in FIG. 6, the acetabular cup removal device for artificial hip joints (hereinafter simply referred to as "acetabular cup removal device") according to an embodiment of the present invention can be mounted on a conventional power tool (P) equipped with a battery, motor, etc.

The acetabular cup removal device of the present invention includes a main shaft (2) and a cutter section (3).

The main shaft (2) can be rotated by the driving force of the power tool (P).

The cutter section (3) is provided at the front end of the main shaft (2), capable of tilting along the acetabulum where the acetabular cup is implanted, and cuts the acetabulum while being rotated by the main shaft (2).

Figure 7:
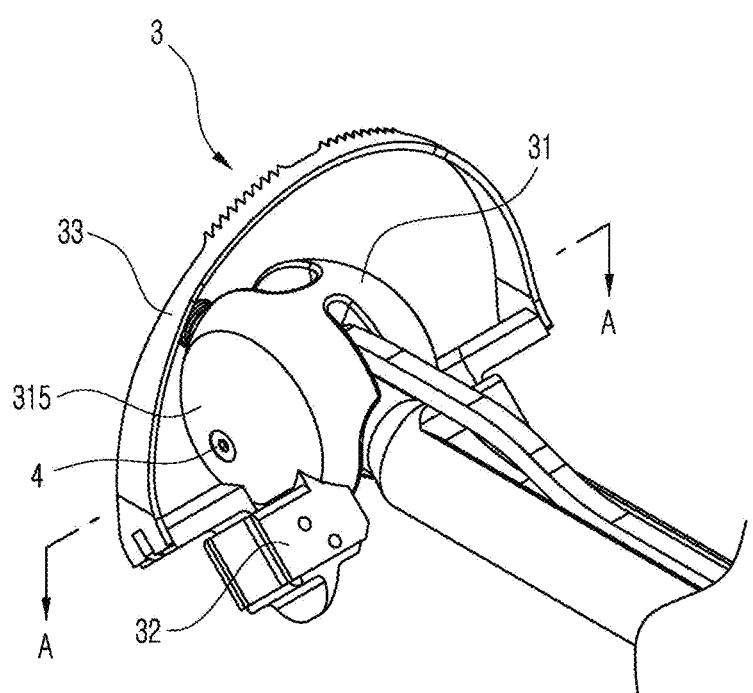
FIG. 7 shows the main components of the cutter section of the acetabular cup removal device in FIG. 6.

As shown in FIG. 7, the cutter section (3) comprises a cutter tilting unit (31), a cutter mounting unit (32), and a cutter (33) detachably mounted on the cutter mounting unit (32).

The cutter tilting unit (31) is capable of tilting along the acetabulum around an imaginary tilting axis (A).

Figure 9:
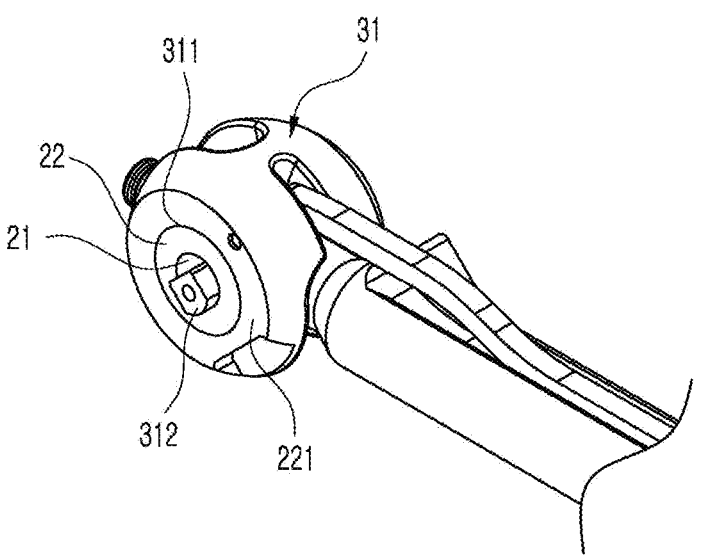
FIG. 9 shows the state where the cutter mounting unit is removed from FIG. 7.
Figure 17:
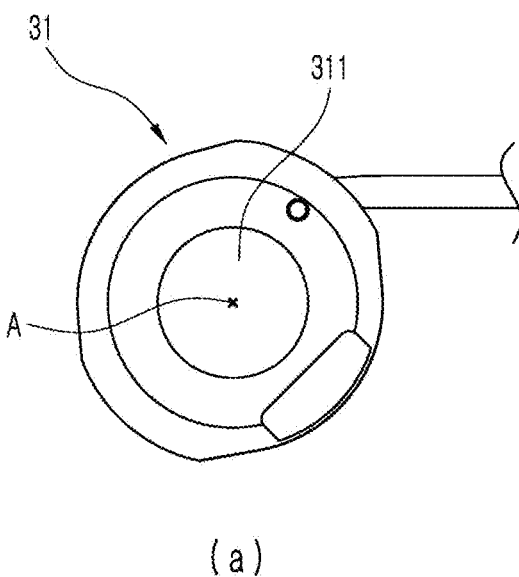
FIG. 17 illustrates the side view (a) and rear view (b) of the cutter tilting unit of the acetabular cup removal device in FIG. 6.
Figure 17:
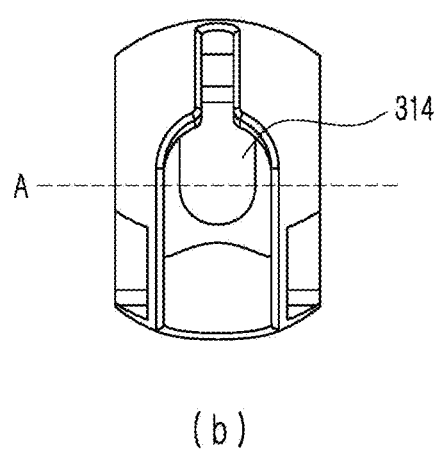
Figure 18:
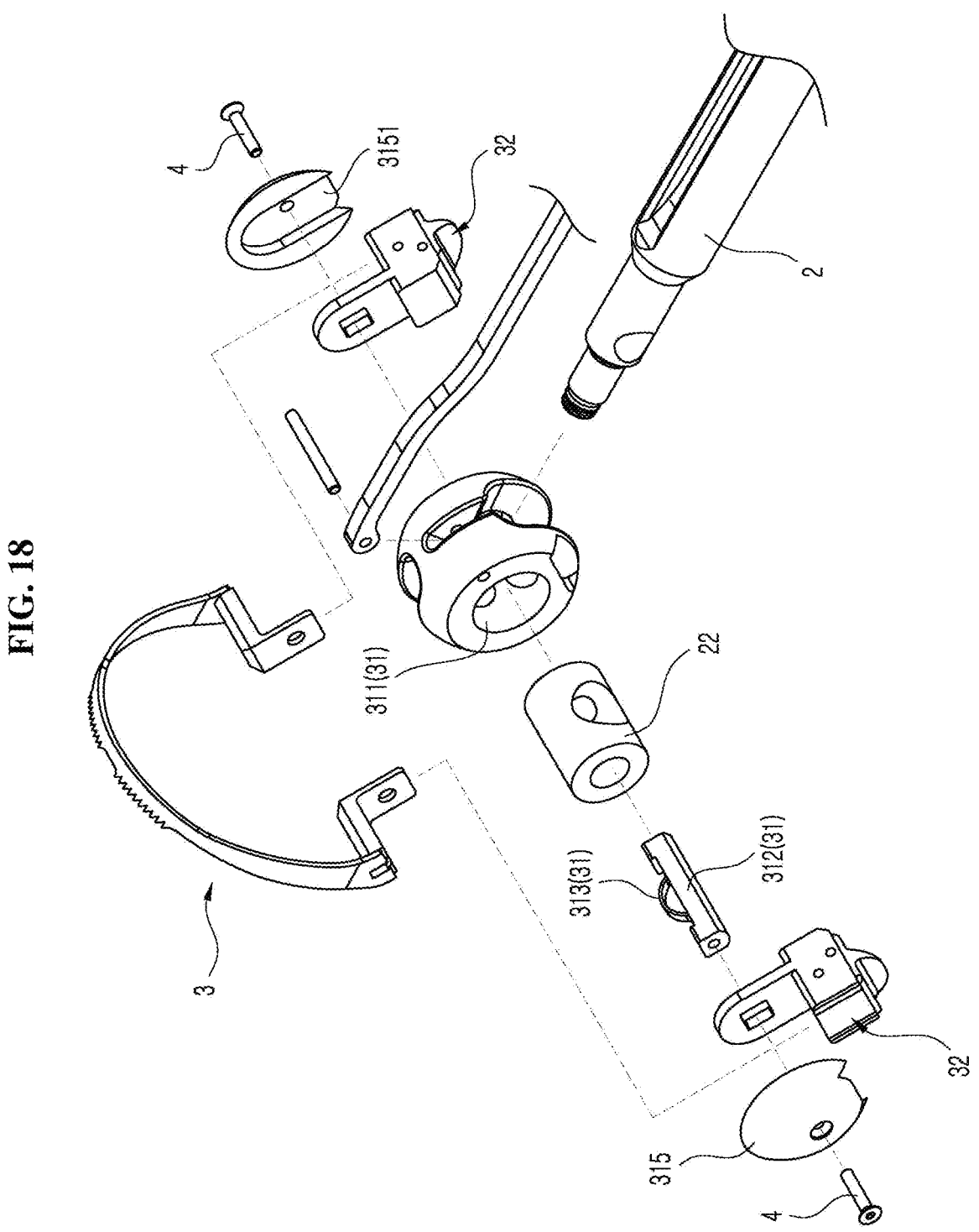
FIG. 18 is an exploded perspective view of the main components of the acetabular cup removal device in FIG. 6.

Specifically, as shown in FIGS. 9, 17, and 18, the cutter tilting unit (31) includes a first through-hole (311), a fourth through-hole (314), a connecting bar (312), and a leaf spring (313).

The first through-hole (311) is formed along the imaginary tilting axis (A), penetrating the cutter tilting unit (31) in the transverse direction (through-plane direction in FIG. 17(a)). And the first through-hole (311) may have a circular cross-section.

The fourth through-hole (314) is formed in a direction perpendicular to the imaginary tilting axis (A), i.e., in the longitudinal direction of the cutter tilting unit (31) (through-plane direction in FIG. 17(b)).

Figure 8:
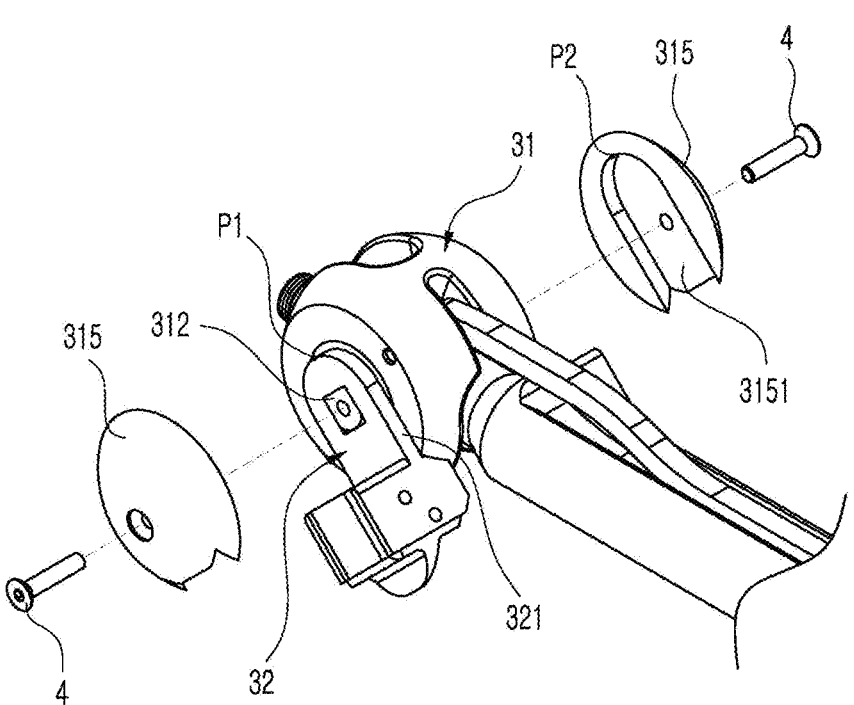
FIG. 8 shows the state where the cover is removed from FIG. 7.

Meanwhile, the main shaft (2) passes through the fourth through-hole (314) of the cutter tilting unit (31) (see FIG. 8). Additionally, the main shaft (2) includes a cylinder member (22) that is inserted into the first through-hole (311) of the cutter tilting unit (31) (see FIGS. 9 and 16).

The cutter tilting unit (31) can rotate relative to the cylinder member (22).

Figure 10:
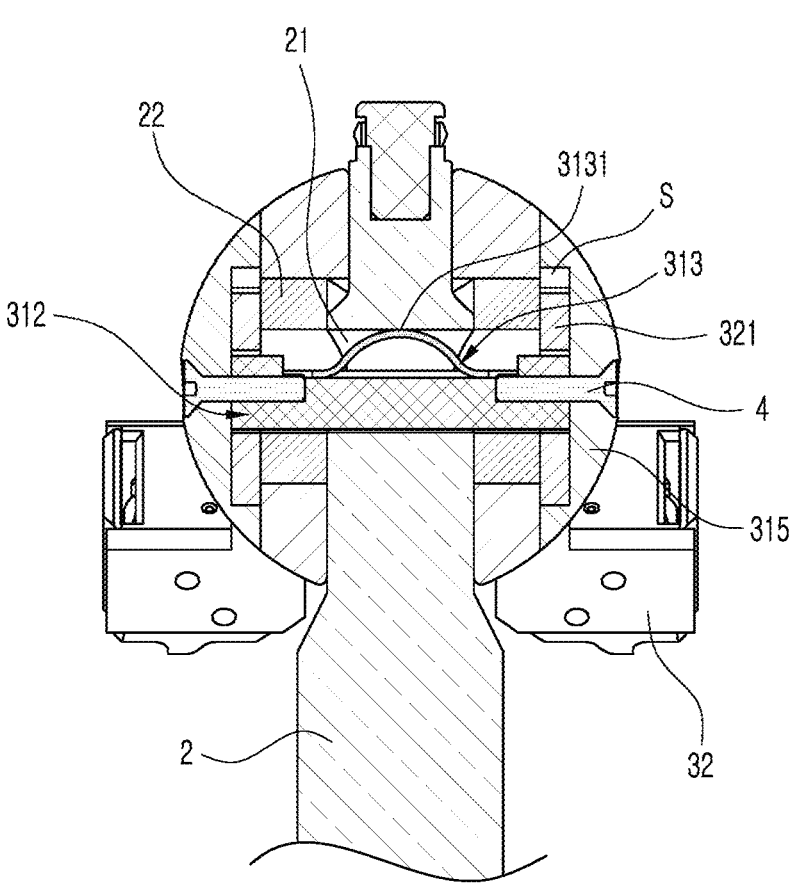
FIG. 10 is a cross-sectional view along the A-A direction of FIG. 7.
Figure 12:
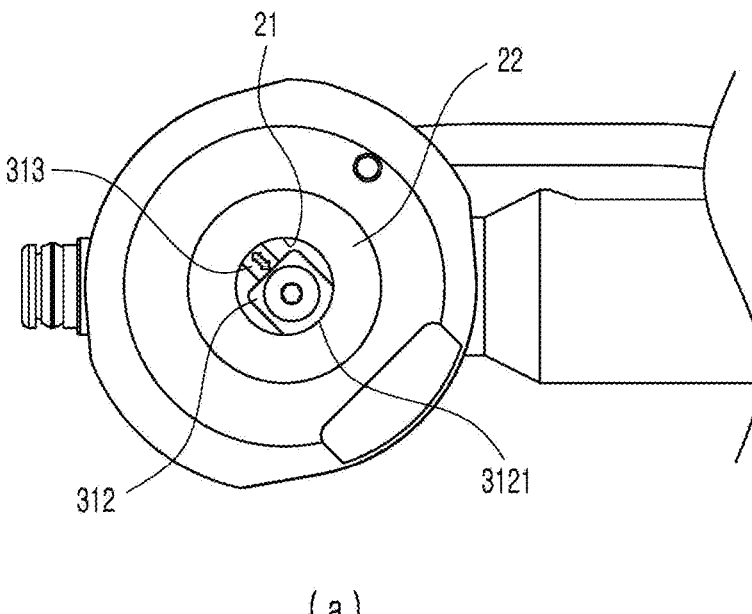
FIG. 12 is a schematic diagram showing the restoring force of the leaf spring acting on the connecting bar in the cutter section of FIG. 6.
Figure 12:
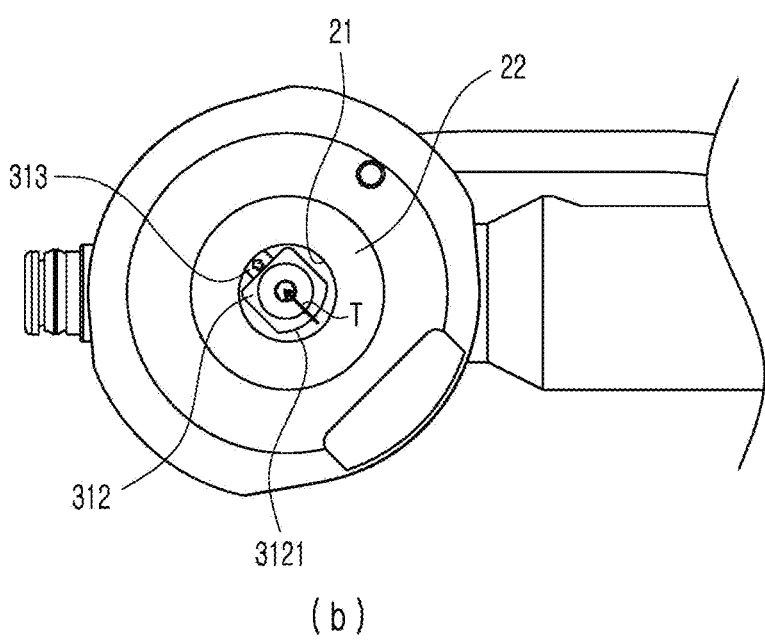
Figure 15:
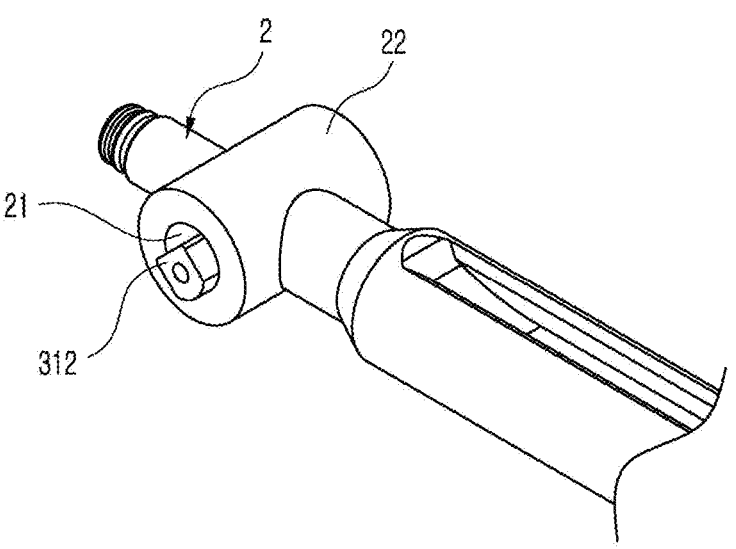
FIG. 15 is a schematic diagram of the main shaft, including the cylinder member, of the acetabular cup removal device in FIG. 6.
Figure 16:
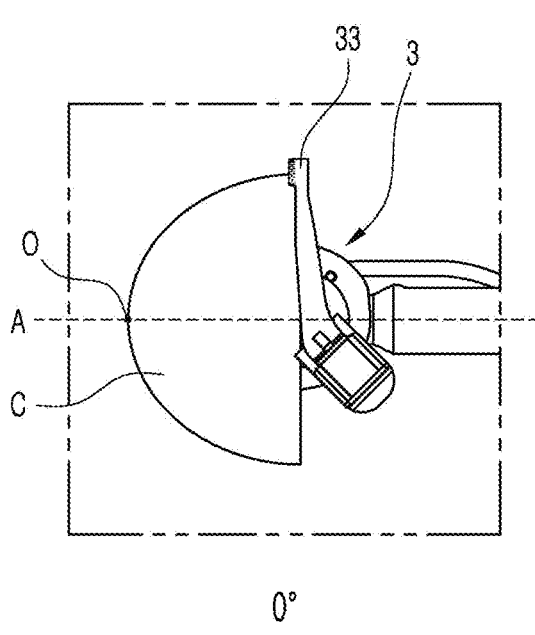
FIG. 16 shows the operation of the acetabular cup removal device in FIG. 6.
Figure 16:
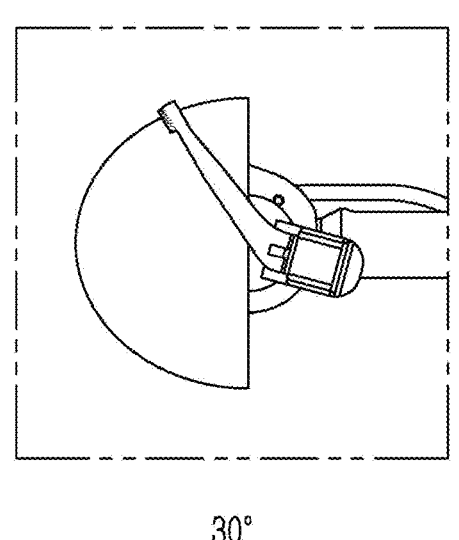
Figure 16:
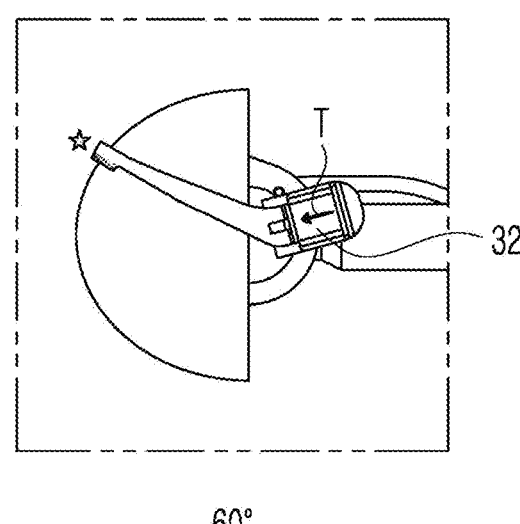
Figure 16:
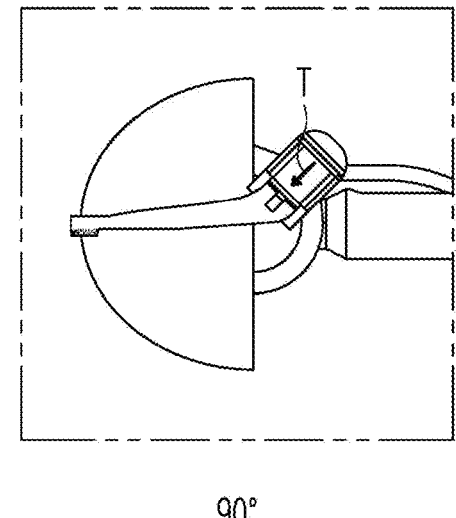

The cylinder member (22) has a second through-hole (21) formed along its longitudinal direction (see FIGS. 10 and 16). As shown in FIGS. 8, 12, and 15, the connecting bar (312) passes through the second through-hole (21) in a manner that allows it to slide toward or away from the tilting axis (A) and is fixed at both ends to the cutter mounting unit (32). Specifically, the connecting bar (312) can slide in the direction of the restoring force (D) exerted by the leaf spring (313) described below, or in the opposite direction due to an external force.

And as shown in FIG. 12, a portion (3121) of the circumference of the connecting bar (312) has an arc shape with a curvature radius matching that of the second through-hole (21), allowing the portion (3121) make surface contact with the inner wall of the second through-hole (21). A remaining portion of the connecting bar (312), except for the portion (3121), does not contact the inner wall of the second through-hole (21).

Figure 11:
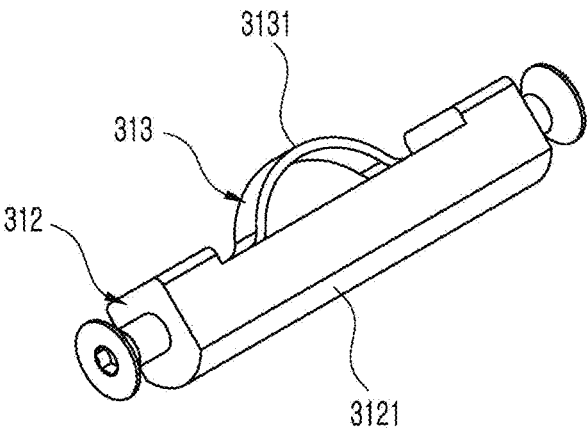
FIG. 11 depicts the connection state of the connecting bar and the leaf spring in the cutter section of FIG. 6.

As shown in FIGS. 10 and 11, the leaf spring (313) is fixed at both ends to the connecting bar (312), with its central portion (3131) supported by the inner wall of the second through-hole (21). As is well known, most leaf springs are made of spring steel and formed in an elliptical shape. Spring steel has the characteristic of bending when pressure is applied to one side but returning to its original position through a damping process.

The cutter mounting unit (32) is coupled to the cutter tilting unit (31) in a manner that allows relative sliding.

Figure 13:
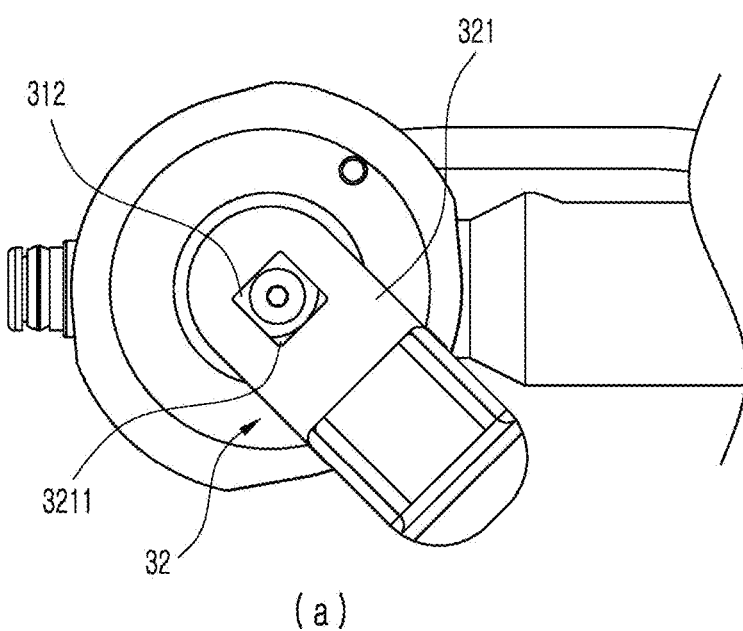
FIG. 13 shows the state where the connecting bar is coupled to the fourth through-hole of the cutter mounting unit in the cutter section of FIG. 6.
Figure 13:
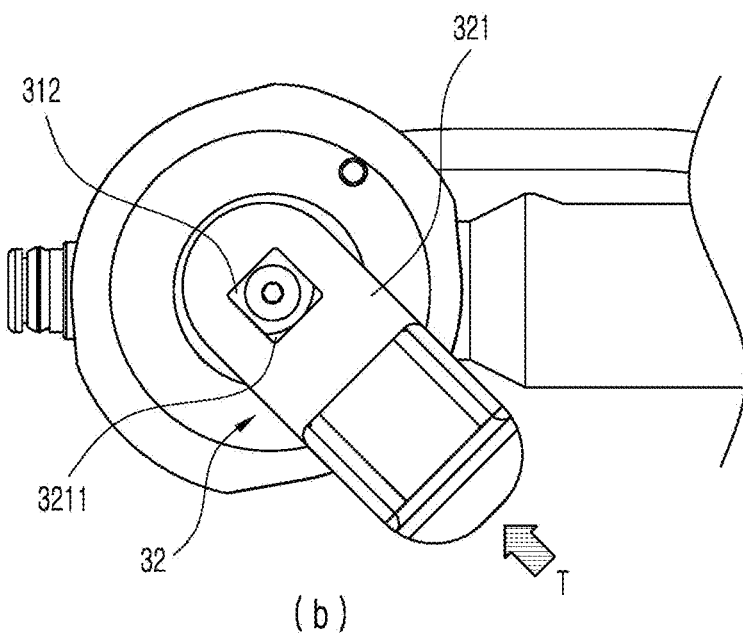

Specifically, as shown in FIG. 13, the cutter mounting unit (32) includes a cutter mounting body (321) provided with a third through-hole (3211) into which the connecting bar (312) is inserted. Here, the connecting bar (312) is fixed within the third through-hole (3211) to prevent relative rotation with respect to the third through-hole (3211). To achieve this, for example, as shown in FIG. 13, the remaining portion of the connecting bar (312), excluding the portion (3121), consists of three straight sides connected at right angles. Correspondingly, the third through-hole (3211) has a rectangular cross-section.

Meanwhile, as shown in FIG. 8, the cutter tilting unit (31) may further include a cover (315) that encloses the cutter mounting body (321) and is fixed to the opposing surface of the cutter tilting unit (31). The cover (315) is secured to the opposing surface of the cutter tilting unit (31) with no relative movement by a fastener (4). On the inner surface of the cover (315), a groove (3151) corresponding to the outline of the cutter mounting body (321) is formed. Through this configuration, when the cutter tilting unit (31) tilts relative to the cylinder member (22), the cover (315) tilts along with it, thereby tilting the cutter mounting unit (32) fixed to the connecting bar (312).

As shown in FIGS. 8 and 10, in the initial state where the connecting bar (312) is not sliding, the cover (315) and the cutter mounting body (321) are arranged so that a gap (S) is formed between the upper end (P1) of the cutter mounting body (321) and the upper end (P2) of the groove (3151) in the cover.

The operation of the acetabular cup removal device for artificial hip joints according to an embodiment of the present invention, having the configuration described above, will be explained below with reference to FIGS. 10 and 16.

Figure 14:
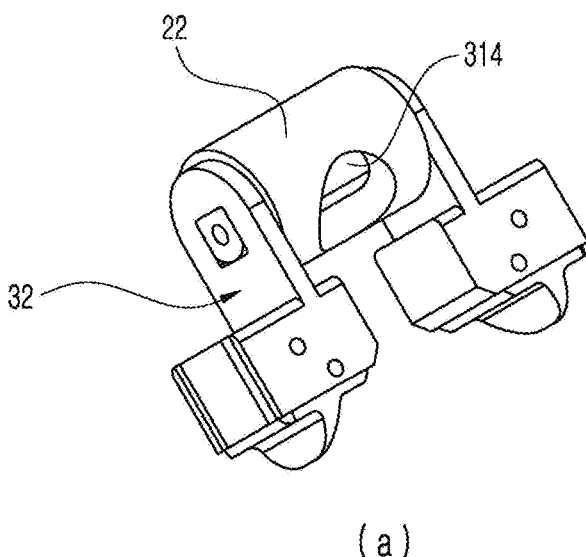
FIG. 14 illustrates the coupling relationship between the cylinder member and the cutter mounting unit of the acetabular cup removal device in FIG. 6.
Figure 14:
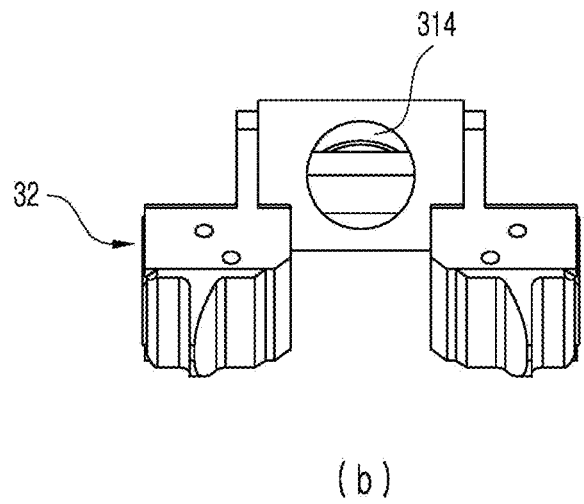

When the acetabular cup (C) is elliptical (a shape cut in half along the minor axis of the ellipse), the cutter section (3) tilts toward the apex (O) of the acetabular cup (C) to remove it from the acetabulum of the pelvis (see 0° and 30° in FIG. 16). At this time, when the cutter section (3) tilts to a predetermined angle, for example, around 60°, the cutter (33) may get caught on the outer surface of the acetabular cup (C). When this occurs, as the cutter section (3) continues to tilt, the reaction force from the contact between the acetabular cup (C) and the cutter (33) applies a pulling force on the cutter mounting unit (32) in the direction where the leaf spring (313) in the second through-hole (21) compresses. This allows the cutter mounting unit (32) to slide in the T direction, as shown in FIGS. 12(b), 13(b), and 14. As a result, the gap(S) between the upper end (P1) of the cutter mounting body (321) and the upper end (P2) of the groove (3151) in the cover narrows. For reference, FIGS. 10 and 13(a) represent the initial state where no external force acts to slide the cutter mounting unit (32).

Thus, unlike conventional devices, the cutter (33) can smoothly traverse the surface of the acetabular cup (C) while tilting the cutter section (3) up to the apex (O) of the acetabular cup (C). This enables the easy removal of the acetabular cup (C) from the acetabulum of the pelvis while minimizing bone loss for the patient (see 90° in FIG. 16).

On the other hand, when the external force acting in the direction that compresses the leaf spring (313) is removed, the cutter mounting unit (32) slides back to its initial state within the second through-hole (21) due to the restoring force (D) of the leaf spring (313) (see FIG. 10). At this time, the gap(S) between the upper end (P1) of the cutter mounting body (321) and the upper end (P2) of the groove (3151) in the cover widens again to its initial state.

While the preferred embodiments of the present invention have been described in detail above, the scope of the present invention is not limited thereto. Various modifications and improvements made by those skilled in the art using the basic concept of the present invention as defined in the following claims also fall within the scope of the present invention.

INDUSTRIAL APPLICABILITY

The present invention can be applied to devices for removing acetabular cups in artificial hip joints.

The invention claimed is:

1. An acetabular cup removal device for artificial hip joints, comprising:
   a main shaft that can be mounted on a power tool and rotated by a driving force of the power tool; and
   a cutter section provided at a front end of the main shaft, capable of tilting along an acetabulum where an acetabular cup is implanted, and cutting the acetabulum while being rotated by the main shaft,
   wherein the cutter section includes:
      a cutter tilting unit capable of tilting along the acetabulum around an imaginary tilting axis,
      a cutter mounting unit coupled to the cutter tilting unit in a manner that allows relative sliding toward or away from the imaginary tilting axis, and
      a cutter detachably mounted on the cutter mounting unit;
   wherein the cutter tilting unit includes:
      a first through-hole penetrating along the imaginary tilting axis,
      a connecting bar fixed at ends of the connecting bar to the cutter mounting unit, and
      a leaf spring fixed at ends of the leaf spring to the connecting bar, with a central portion between the ends of the leaf spring;
   wherein the main shaft includes:
      a cylinder member inserted into the first through-hole and having a second through-hole formed along a longitudinal direction of the cylinder member;
   wherein the connecting bar is positioned within the second through-hole and is capable of sliding toward or away from the imaginary tilting axis, and
   wherein the central portion of the leaf spring is supported by an inner wall of the second through-hole.

2. The acetabular cup removal device for artificial hip joints according to claim 1, wherein the second through-hole has a circular cross-section, and a portion of a circumference of the connecting bar has an arc shape with a curvature radius identical to a curvature radius of the second through-hole, allowing the portion of the circumference of the connecting bar to make contact with the second through-hole.

3. The acetabular cup removal device for artificial hip joints according to claim 2, wherein a remaining portion of the connecting bar, except for the portion that contacts the second through-hole, does not contact the second through-hole.

4. The acetabular cup removal device for artificial hip joints according to claim 3, wherein the cutter mounting unit includes a cutter mounting body provided with a third through-hole into which the connecting bar is inserted, and the connecting bar does not rotate relative to the cutter mounting body within the third through-hole and tilts in conjunction with tilting of the cutter mounting unit.

5. The acetabular cup removal device for artificial hip joints according to claim 4, wherein a remaining portion of the connecting bar consists of three sides connected at right angles, and the third through-hole has a rectangular cross-section.

6. The acetabular cup removal device for artificial hip joints according to claim 4, wherein the cutter tilting unit further includes a cover that encloses the cutter mounting body and is fixed to an opposing surface of the cutter tilting unit.

7. The acetabular cup removal device for artificial hip joints according to claim 6, wherein a groove corresponding to an outline of the cutter mounting body is formed on an inner surface of the cover, and a gap is formed between an upper end of the cutter mounting body and an upper end of the groove in the cover.

8. The acetabular cup removal device for artificial hip joints according to claim 6, wherein the cover is fixed to the opposing surface of the cutter tilting unit with no relative movement by a fastener secured to the connecting bar.

9. The acetabular cup removal device for artificial hip joints according to claim 2, wherein, in an initial state where no external force acts on the leaf spring, the portion of the connecting bar contacts the second through-hole, and when external force acts on the leaf spring, the leaf spring compresses, causing the portion of the connecting bar to separate from the second through-hole.

* * * * *